United States Patent [19]

Mues et al.

[11] 4,167,405
[45] * Sep. 11, 1979

[54] FERTILIZERS FOR SUPPLYING PLANTS WITH IRON

[75] Inventors: Volker Mues, Wuppertal; Johannes Niggemann, Leverkusen, both of Fed. Rep. of Germany

[73] Assignee: Bayer Aktiengesellschaft, Leverkusen, Fed. Rep. of Germany

[*] Notice: The portion of the term of this patent subsequent to Oct. 11, 1994, has been disclaimed.

[21] Appl. No.: 865,479

[22] Filed: Dec. 29, 1977

[30] Foreign Application Priority Data

Jan. 22, 1977 [DE] Fed. Rep. of Germany ....... 2702628

[51] Int. Cl.$^2$ .............................................. C05F 11/00
[52] U.S. Cl. .................................. 71/27; 71/DIG. 2; 260/439 CY
[58] Field of Search ..................... 71/1, DIG. 2, 27; 260/439 CY

[56] References Cited

U.S. PATENT DOCUMENTS 4,053,296  10/1977  Mues et al. ........................... 71/D 2

FOREIGN PATENT DOCUMENTS 2553786  6/1977  Fed. Rep. of Germany ........... 71/D 2

Primary Examiner—Joseph Scovronek
Assistant Examiner—Chris Konkol
Attorney, Agent, or Firm—Sprung, Felfe, Horn, Lynch & Kramer

[57] ABSTRACT

A method of supplying plants with iron which comprises applying to the plants, or to the substrate in which they grow, at least one ferrocene derivative of the formula

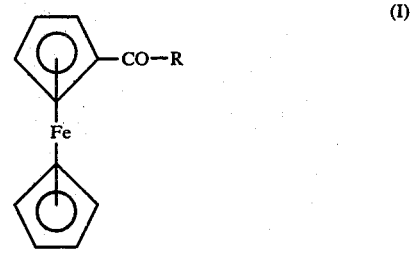

wherein R represents alkyl with 3 to 20 carbon atoms, preferably 7 to 20 carbon atoms, alone or in admixture with a diluent or carrier.

7 Claims, No Drawings

FERTILIZERS FOR SUPPLYING PLANTS WITH IRON

BACKGROUND OF THE INVENTION

The present invention relates to the use as fertilizers of certain ferrocene derivatives, some of which are known, and especially to their use for the prevention and cure of iron deficiency diseases in plants.

It has already been disclosed that ferrocene derivatives can be used for treating iron deficiency anaemias in humans and animals and as antioxidants, anti-knock agents, additives for motor fuels and oils, color pigments, radiation absorbers, insecticides and fungicides (see British patent specification No. 898,633, U.S. Pat. Nos. 3,432,533, 3,535,356, 3,553,241 and 3,557,143, German Offenlegungsschriften (German Published Specification) Nos. 2,107,657, 2,453,936 and 2,453,967 and U.S.S.R. patent specification 400,597).

It is also known to prevent or cure iron deficiency diseases in plants by adding water-soluble iron salts, for example iron sulphate, to the substrate in which the plants grow. Using such conventional agents, it is indeed possible to supply the plants with iron in weakly acid substrates or in substrates having a neutral reaction. However, their use in soils having a weakly basic reaction suffers from considerable disadvantages. Thus, in weakly alkaline substrates, the iron ions cannot be taken up by the plants at all or can be taken up only in an insufficient amount because these ions then separate out in the form of sparingly soluble hydroxides and therefore do not contribute to plant nutrition.

Furthermore, it is known that, if needed, the plants can be supplied with iron in the form or iron chelate complexes of citric acid, gluconic acid, nitrilotriacetic acid, ethylenediaminetetracetic acid and ethylenediamine-N,N'-di-(o-hydroxyphenyl)-acetic acid. See "Der Vegetationsversuch" ("Vegetation Experiments") in "Methodenbuch" ("Book of Methods"), Volume VIII, Neumann Verlag, Radebeul, Berlin, 1951, 180 to 194; Plant Physiology 26, 411 (1951); Soil Science 80, 101 to 108 (1955) and "Organic Sequestering Agents", John Wiley and Sons, Inc., New York, 1959, 455 to 469.

With the aid of such iron complexes it is possible to supply the plants with iron not only in weakly acid or neutral soils but also, to a certain degree, in weakly alkaline soils because, as a result of the relatively high stability of these complexes, an undesired precipitation of the iron cations in the neutral or weakly basic medium is largely prevented. Nevertheless, the use of iron chelate complexes for the indicated purpose suffers from some disadvantages. Thus, the duration of action of iron chelate complexes of citric acid or gluconic acid is only relatively short, since these naturally occurring acids can be degraded relatively rapidly by soil microorganisms. The iron chelate complexes of the synthetic aminopolycarboxylic acids with the exception of the iron complex of ethylenediamine-N,N'-di-(o-hydroxyphenyl)-acetic acid, which is important for combating chlorosis, can be employed only with certain limitations in strongly alkaline soils because the stability of the complexes does not always suffice to avoid the iron cations being immobilised in the form of sparingly soluble hydroxides or oxides. A further disadvantage is that the aminopolycarboxylic acids form very stable, highly toxic and at the same time water-soluble chelate complexes with the heavy metal ions of cadmium, lead and mercury, which can be present in the soil in the form of almost insoluble compounds. Since these heavy metal ion complexes can, because of their good solubility, pass into the soil water, the use of aminopolycarboxylic acids is not without risk for toxicological reasons. It is true that the iron complex of ethylenediamine-N,N'-di-(o-hydroxyphenyl)-acetic acid is, as already mentioned, of practical importance in combating chlorosis; however, it is a disadvantage that this compound can be prepared only with relative difficulty and is furthermore not light-stable.

SUMMARY OF THE INVENTION

It has now been found that ferrocene derivatives, some of which are known, of the general formula

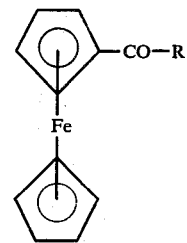

(I)

in which R represents alkyl with 3 to 20 carbon atoms, are very suitable for supplying plants with the micronutrient iron.

Accordingly, the present invention provides a method of supplying plants with iron, which comprises applying to the plants, or to the substrate in which they grow, at least one ferrocene derivative of the formula (I) above, alone or in admixture with a diluent or carrier.

The outstanding activity of the substance to be used according to the invention in supplying plants with iron is to be regarded as very surprising since it was to be assumed, in the light of the known state of the art, that the substances to be used according to the invention are only of poor suitability for the stated purpose because, compared with the aminopolycarboxylic acids, they contain iron in a very highly complexed form. Contrary to expectations, however, the substances according to the invention possess a very good activity in micronutrient fertilization. It is particularly advantageous that the substances to be used according to the invention do not form stable complexes with the heavy metal ions of cadmium, lead and mercury present in the soil. Hence, use of ferrocene derivatives for supplying plants with iron is safe on toxicological grounds. In addition, the ferrocene derivatives according to the invention are not only able to ensure an outstanding supply to the plant via the roots but, in contrast to all of the iron complexes described hitherto, are also able to provide an extremely efficient supply of iron by application to the leaves and in this way (which was not possible hitherto) contribute to plant nutrition and to the prevention and cure of iron deficiency diseases in plants. The invention thus represents a valuable enrichment of the art.

The formula (I) provides a general definition of the ferrocene derivatives which can be used according to the invention. In the formula (I), R preferably represents straight-chain or branched alkyl with 7 to 20 carbon atoms.

Examples which may be mentioned of the ferrocene derivatives of the formula (I) which can be used according to the invention are: iso-butyrylferrocene, trimethylacetoferrocene, n-pentanoylferrocene (valeroylferrocene), isopentanoylferrocene, sec.-pentanoylferrocene, n-hexanoylferrocene (caproyl-ferrocene), n-heptanoylferrocene, n-octanoylferrocene (capryloyl-ferrocene), 2-ethylhexanoylferrocene, n-nonaoylferrocene, n-decanoylferrocene (caprinoyl-ferrocene), n-undecanoylferrocene, n-dodecanoylferrocene (lauroylferrocene), n-tridecanoylferrocene, n-tetradecanoylferrocene (myristoylferrocene), n-pentadecanoylferrocene, n-hexadecanoylferrocene (palmitoylferrocene), n-heptadecanoylferrocene, n-octadecanoylferrocene (stearoylferrocene), n-nonadecanoylferrocene and n-eicosanoylferrocene.

Mixtures of ferrocene derivatives of the formula (I) and mixtures which are obtained by acylating ferrocene with coconut oil acid chloride, versatic acid chloride isononanoic acid chloride, edonoxoic acid chloride or naphthenic acid chloride can also be used according to the invention.

Some of the ferrocene derivatives of the formula (I) which can be used according to the invention are known (see "Organic Reactions", Volume 17, Chapter 1, page 1 to 151).

Certain individual ferrocene derivatives which can be used according to the invention have not hitherto been described in the literature, but they can be prepared in a simple manner by processes which are known in principle.

The ferrocene derivatives of the formula (I) which can be used according to the invention are obtained, for example, when ferrocene is reacted
(a) with an acyl chloride of the general formula

$$R-CO-Cl \quad (II),$$

in which R has the meaning stated above, or
(b) with an acid anhydride of the general formula

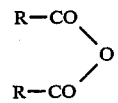

$$\begin{array}{c} R-CO \\ \phantom{R-CO}\diagdown \\ \phantom{R-CO-}O \\ \phantom{R-CO}\diagup \\ R-CO \end{array} \quad (III),$$

in which R has the meaning stated above, optionally in the presence of a solvent, such as, for example, methylene chloride or ethylene chloride, and in the presence of a Friedel-Crafts catalyst, such as, for example, aluminium chloride, zinc chloride, boron trifluoride, hydrogen fluoride or phosphoric acid, at temperatures between 0° C. and 100° C.

The ferrocene derivatives of the formula (I) can be used with particular advantage for fertilizing via the leaves since they can be absorbed well by the leaves. The ferrocene derivatives of the formula (I) can therefore be employed for preventing and for curing iron deficiency diseases in plants. In many cases it is possible to achieve a successful cure even when the disease is in an advanced stage.

The plants which are prone to iron deficiency diseases (iron deficiency chloroses) include: species of cereals (for example, rice, maize and millet), tuber and root crops (for example sugar beet), oleaginous fruits (for example soya bean, groundnut, olive and sunflower), table fruit (for example peach, pear, apple, apricot, plum, cherry, quince, citrus fruit, grape, hazelnut, walnut, currant, gooseberry, raspberry, blackberry, bilberry, pineapple and avacado), vegetables (for example lettuce, broad bean, pea, tomato and melon), decorative trees and shrubs (for example rose, eucalyptus, liquidamber, mimosa, elm, catalpa, spirea, pyracantha, juniperus, ligustrum, hibiscus, syringa and hydrangea), perennials (for example delphinium, primula, paenia, poppy, anthirrhinum, iris and lupine), pot plants and annuals (for example pelargonium, petunia, gardenia, calceolaria, chrysanthemum, camellia and begonia), peat-loving plants (for example azalea, rhododendron, erica and skimmia) and grasses (for example lawn grasses).

The ferrocene derivatives to be used according to the invention can be converted into the usual formulations, such as solutions, emulsions, suspensions, powders, pastes and granules. These may be produced in known manner, for example by mixing the active compounds with extenders, that is to say, liquid or solid or liquefied gaseous diluents or carriers, optionally with the use of surface-active agents, that is to say, emulsifying agents and/or dispersing agents and/or foaming agents. In the case of the use of water as an extender, organic solvents can, for example, also be used as auxiliary solvents.

As liquid diluents or carriers, especially solvents, there are suitable in the main, aromatic hydrocarbons, such as xylene, toluene, benzene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperatures and under normal pressure, for example aerosol propellants, such as dichlorodifluoromethane or trichlorofluoromethane.

As solid carriers there are preferably used ground natural minerals, such as kaolins, clays, talc, chalk, quartz, attapulgite, montmorillonite or diatomaceous earth, and ground synthetic minerals, such as highly dispersed silicic acid, alumina and silicates.

Preferred examples of emulsifying and foam-forming agents include nonionic and anionic emulsifiers, such as polyoxyethylene-fatty acid esters, polyoxyethylene-fatty alcohol ethers, for example alkylaryl polyglycol ethers, alkyl sulphonates, alkyl sulphates and aryl sulphonates as well as albumin hydrolysis products; and preferred examples of dispersing agents include lignin sulphite waste liquors and methylcellulose.

The compounds to be used according to the invention for supplying plants with iron can be present in the formulations as a mixture with other fertilizers or pesticidal active compounds. The formulations in general contain from 0.1 to 95% by weight of active compound, preferably from 0.5 to 90% by weight.

The active compounds can be used as such, in the form of their formulations or as the use forms prepared therefrom, such as ready-to-use solutions, emulsions, foams, suspensions, powders, pastes and granules. They may be used in accordance with the methods customary in agriculture and in horticulture, for example by direct introduction into the soil, by watering, spraying, atomising, scattering or dusting. The following may be mentioned as special types of application: root application, leaf application, stem injection and bark application. In the case of root application, the fertilizer can either be mixed with the culture substrate or be introduced into furrows in the soil. Furthermore, it is possible to introduce the fertilizer into the lower root region by means of a fertilizer lance or through punched or drilled holes. Application to the leaf is, as a rule, effected by spraying the plants with a fertilizer solution or dipping plants or parts of plants into a fertilizer solution. In the case of stem injection, the fertilizer is directly introduced into the plants through bore-holes, particularly in tree trunks or branches. Bark application can be effected by spraying the bare wood with the fertilizer solution, or by placing bands of paper, textile or foam plastic, impregnated with nutrient, on tree trunks or branches - if appropriate after partial or complete removal of the layer of bark or cork in the treatment zone. Application to the bark by means of pastes containing nutrient is also possible.

It is also possible to apply the ferrocene derivatives according to the invention by the ultra-low-volume (ULV) method.

The amount of the ferrocene derivative which is employed can be varied within a substantial range. It depends essentially on the nature of the soil and on the nutrient requirement of the particular plant. In general, the amounts of active compound used are from 0.1 to 100 kg/ha and preferably from 1 to 50 kg/ha.

The ferrocene derivatives according to the invention are very suitable for combating and curing iron deficiency diseases in plants. Thus, for example in the case of completely chlorotic chrysanthemums (*Chrysanthemum indicum*; variety: Yellow Delaware) the iron deficiency can be greatly reduced or even completely cured by treating the plants with the ferrocene derivatives according to the invention.

The good activity of the ferrocene derivatives to be used according to the invention in supplying plants with iron can be seen from the Example which follows.

In this Example, the ferrocene derivatives of the formula (I) are each identified by the number (given in brackets) of the corresponding preparative Example which will be found later in this text.

The known comparison preparation is identified as follows:

"Fetrilon" = a commercially available iron fertilizer based on an iron chelate complex of the sodium salt of ethylenediaminetetra-acetic acid

EXAMPLE A

Combating iron deficiency/leaf uptake test

Test plant: *Chrysanthemum indicum* (Variety: Yellow Delaware)

Culture substrate: Mixture of polystyrene foam flock (Styromull) and potassium alginate in the volume ratio of 10:1

To prepare a suitable formulation of the active compound, the particular amount of active compound desired was dissolved in water. In the case of active compounds which had a low solubility in water the active compound formulation was prepared by dissolving 1 g of the active compound in 10 ml of a formulation mixture consisting of 47 parts by volume of dimethylformamide, 47 parts by volume of acetone and 6 parts of an alkylaryl polyglycol ether (emulsifier), and then diluting the concentrate, thus obtained, with water to the desired concentration.

Test plants were grown in a culture substrate of the composition indicated above, fertilization and watering being effected by adding, twice weekly, a mineral-iron-deficient nutrient solution according to Hoagland and Arnon (Circular 347, College of Agriculture, University of California, Berkeley 1950). The completely chlorotic test plants grown in this way were sprayed, in the five-leaf stage, with the active compound formulation until dripping wet, using covers to ensure that the active compound formulation did not enter the culture substrate. After 2 days the plants were again sprayed with the active compound formulation in the same manner.

The evaluation took place when an average of 2 leaves had newly formed on the plants treated with an optimum amount of a water-soluble, commercially available iron fertilizer, in each case, the average number of newly formed leaves was determined on all test plants. Furthermore, the intensity of the green colour of newly formed leaves was rated and expressed as a numerical code.

In this, the figures denoted:
1 = 0% chlorotic (dark green)
3 = 25% chlorotic
5 = 50% chlorotic
7 = 75% chlorotic
9 = 100% chlorotic (corresponding to the untreated control plants)

The active compound, the active compound concentrations and the experimental results can be seen from the table which follows:

Table A

Combating iron deficiency/leaf uptake test
Test plant: *Chrysanthemum indicum*/Variety: Yellow Delaware

| Iron Compound in the nutrient preparation | Water solubility of the preparation | Nutrient preparation in the spray liquor [%] | Intensity of the green colour of young leaves | Average number of newly formed leaves |
|---|---|---|---|---|
| — (control) | — | — | 9 | 0 |
| "Fetrilon" | complete | 0.2 | 4 | 2 |
| (2) | slight | 0.03 | 3 | 4 |
|  |  | 0.16 | 2-3 | 5 |
|  |  | 0.78 | 2 | 5 |
| (7) | slight | 0.03 | 3 | 4 |
|  |  | 0.15 | 2-3 | 5 |
|  |  | 0.74 | 2 | 5 |
| (6) | slight | 0.03 | 3 | 4 |
|  |  | 0.14 | 2-3 | 5 |
| (5) | slight | 0.13 | 3 | 4 |
|  |  | 0.66 | 2-3 | 4 |
| (4) | slight | 0.13 | 3 | 3 |
|  |  | 0.62 | 2-3 | 3 |
| (3) | slight | 0.12 | 2-3 | 4 |
|  |  | 0.59 | 2 | 4 |

Preparative Examples

EXAMPLE 1

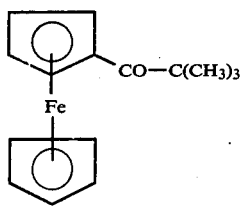

A mixture of 0.5 mole of ferrocene, 250 ml of trimethylacetic anhydride and 20 ml of 85% strength phosphoric acid was heated to 100° C. for 10 minutes, then cooled and poured on to ice. After allowing the reaction mixture to stand overnight, it was extracted with methylene chloride. The organic phase was washed with water, dried and distilled under a high vacuum. In this manner, 44 g (33% of theory) of trimethylaceto-ferrocene with a boiling point of 145° C./3 mm Hg were obtained

EXAMPLE 2

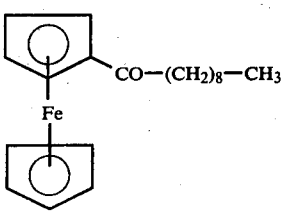

A solution of 0.5 mole of capric acid chloride in 150 ml of ethylene chloride was added dropwise to a suspension of 0.5 mole of aluminum chloride in 500 ml of ethylene chloride at 20° C., whilst cooling slightly. This suspension was added dropwise to a solution of 0.5 mole of ferrocene in 750 ml of ethylene chloride at 0° C.-5° C., whilst cooling. The reaction mixture was stirred overnight at room temperature, then heated under reflux for 20 minutes, subsequently cooled and poured into ice-water. The organic phase was separted off, washed with water until neutral and dried. Thereafter, the solvent was stripped off and the residue was distilled under reduced pressure. In this manner 95 g (56% of theory) of n-decanoyl-ferrocene, which boiled between 205° C. and 210° C. at 1 mm Hg, were obtained.

The compounds listed in the Table 1 which follows were obtained by procedures analogous to that described in Example 2.

Table 1

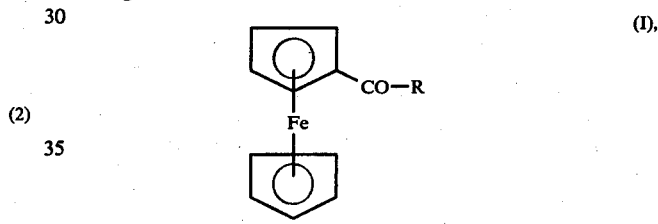

| Example No. | R | Boiling point or melting point [in each case in °C.] | Yield (% of theory) |
|---|---|---|---|
| 3 | $C_4H_9$-n | 166–170/1 mm Hg | 55 |
| 4 | $C_5H_{11}$-n | 173–178/1 mm Hg | 48 |
| 5 | $C_6H_{13}$-n | 181–186/1 mm Hg | 59 |
| 6 | $C_7H_{15}$-n | 187–190/1 mm Hg | 51 |
| 7 | $C_8H_{17}$-n | 190–195/1 mm Hg 39 | 44 |
| 8 | $C_3H_7$-iso | 128–132/1 mm Hg | 43 |
| 9 | $C_4H_9$-iso | 170–173/3 mm Hg | 58 |
| 10 | $C_4H_9$-sec. | 135/1 mm Hg | 34 |
| 11 | $C_{17}H_{35}$-n | 80 | 28 |
| 12 | $-CH(C_2H_5)-C_4H_9$-n | 156–159/1 mm Hg | 60 |

What we claim is:

1. A method of supplying plants with iron, which comprises applying to the plants, or to the substrate in which they grow, at least one ferrocene derivative of the general formula

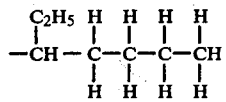

(I), in which
R represents alkyl with 7 to 20 carbon atoms, alone or in admixture with a diluent or carrier.

2. A method according to claim 1 wherein in said ferrocene derivative R is n-heptyl.

3. A method according to claim 1 wherein in said ferrocene derivative R is n-octyl.

4. A method according to claim 1 wherein in said ferrocene derivative R has the formula $$-CH(C_2H_5)-\underset{H}{\overset{H}{C}}-\underset{H}{\overset{H}{C}}-\underset{H}{\overset{H}{C}}-CH_H$$

5. A method according to claim 1 wherein said ferrocene derivative is applied in an amount of from 0.1 to 100 kg per hectare.

6. A method according to claim 5 wherein said ferrocene derivative is applied in an amount of from 1 to 50 kg per hectare.

7. The method according to claim 1 in which the ferrocene derivative is applied to a plant suffering from iron deficiency disease.

* * * * *